United States Patent [19]

Chang et al.

[11] 4,433,059

[45] Feb. 21, 1984

[54] DOUBLE ANTIBODY CONJUGATE

[75] Inventors: Chi-Deu Chang, Bridgewater; Henry A. Graham, Jr., Annandale, both of N.J.

[73] Assignee: Ortho Diagnostic Systems Inc., Raritan, N.J.

[21] Appl. No.: 299,764

[22] Filed: Sep. 8, 1981

[51] Int. Cl.³ .................. G01N 33/54; G01N 33/58; G01N 33/60

[52] U.S. Cl. .................. 436/512; 436/528; 436/540; 436/814; 436/820; 436/823; 436/824; 436/520

[58] Field of Search .............. 424/1; 436/512, 518, 436/519, 520, 528, 540, 808, 814, 820, 823, 824

[56] References Cited

U.S. PATENT DOCUMENTS

| | | | |
|---|---|---|---|
| 3,882,225 | 5/1975 | Patel et al. | 424/12 |
| 4,007,089 | 2/1972 | Smith | 260/112 R X |
| 4,189,464 | 2/1980 | Blumberg et al. | 424/1 |
| 4,189,466 | 2/1980 | Ainis et al. | 424/12 |
| 4,200,436 | 4/1980 | Mochida et al. | 424/1 |
| 4,286,964 | 9/1981 | Seed | 424/1 |
| 4,292,403 | 9/1981 | Duermeyer | 424/1 |
| 4,331,647 | 5/1982 | Goldenberg | 424/1.1 |
| 4,342,566 | 8/1982 | Theofilopoulos et al. | 424/1 |

OTHER PUBLICATIONS

Pain et al., J. Immunological Methods 40(1981), 219–230.
Kitagawa et al., Chem. Abstracts, 91(1979) #204049m.

*Primary Examiner*—Christine M. Nucker
*Attorney, Agent, or Firm*—Mark A. Hofer

[57] ABSTRACT

Reagents and methods are described for an immunoassay test of increased sensitivity and decreased complexity employing an immunoglobulin specific for an antigen naturally or artificially placed upon the surface of an indicator particle coupled through the use of a hetero-bifunctional coupling reagent to a second antibody of differing specificity and specific for the antigen to be detected. In a preferred embodiment, a hetero-bifunctional coupling agent couples via a sulfhydryl group, a univalent immunoglobulin specific for the surface antigens on erythrocytes to a second multivalent immunoglobulin through an amide linkage with the latter immunoglobulin wherein said second immunoglobulin is specific for hepatitis-B surface antigen.

23 Claims, 4 Drawing Figures

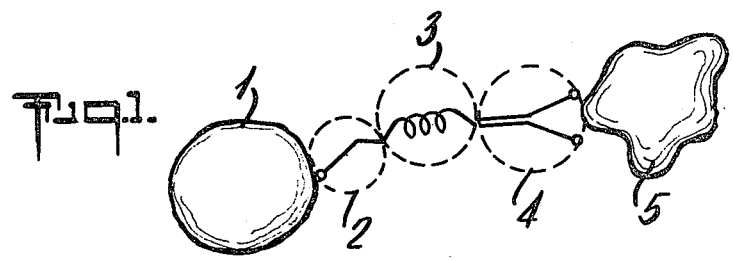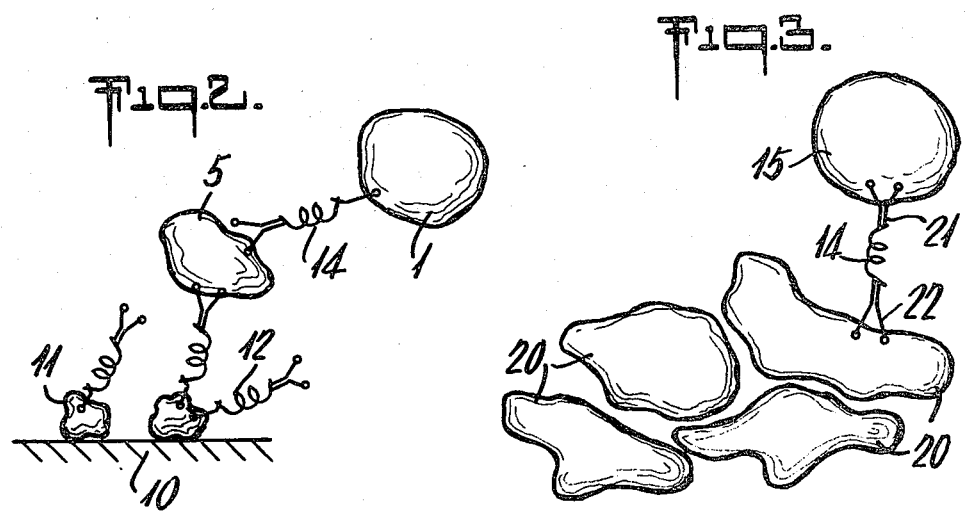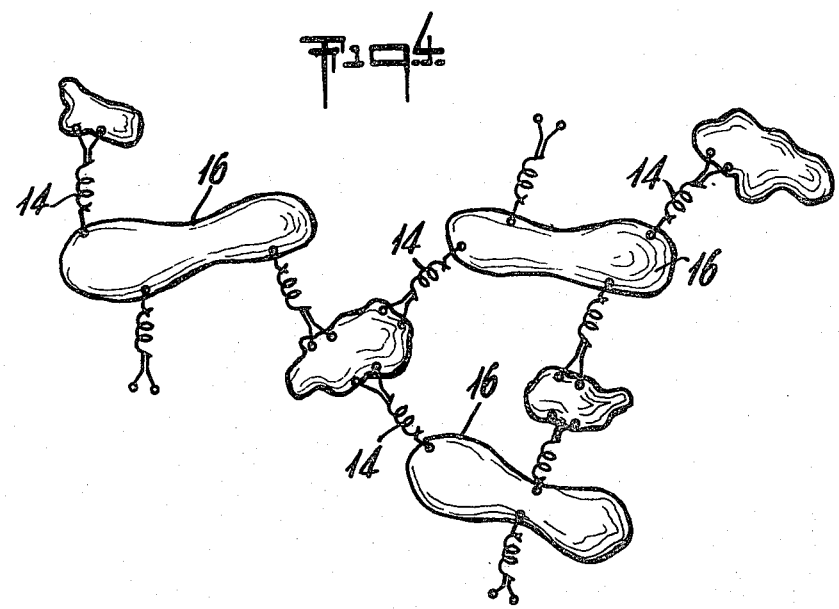

DOUBLE ANTIBODY CONJUGATE

FIELD OF THE INVENTION

This invention relates to the field of immunoassays and more specifically describes an immunoassay reagent formed by the coupling of immunoglobulins of differing specifities by the use of a hetero-bifunctional coupling reagent.

BACKGROUND OF THE INVENTION

The invasion of the human body by microbial substances and the resulting infection is often difficult to diagnose because of diverse or minimal pathological effects. Immunology, the study of immune responses to the introduction of foreign substances to the body, concerns itself with two classes of macromolecules. These classes, antigens and antibodies, react in specific manners. The foreign invading substance or antigen has generally two properties associated with it, immunogenicity, the capacity to stimulate the formation of a corresponding antibody, and the ability to react specifically with those antibodies. The antibody itself is a protein that is formed in response to the presence of an antigen for reaction with that specific antigen. Antibodies belong to a special group of serum proteins called immunoglobulins. Although the group of antibodies comprises a restricted group of proteins that are capable of specifically reacting with antigens, there is an enormous variety of macromolecules capable of behaving as antigens including proteins, many polysaccharides, nucleoproteins, lipoproteins, numerous synthetic polypeptides as well as many other small molecules when they are suitably linked to proteins or synthetic polypeptides.

The specificity of antibody-antigen reactions has been utilized in the diagnosis of pathological states or physiological conditions and more particularly, in the determination of the presence of antigenic determinants, i.e. those restricted portions of the antigen molecule that determine the specificity of antibody-antigen reactions. In accordance with the knowledge of those skilled in the art, antigen-antibody reactions can be manifested by enzyme immunoassay (EIA), radioimmunoassay (RIA), or immunofluorescence (IF) techniques with high sensitivity, however, these techniques are complex and generally require great skill, time and complex electronic instruments.

Typically, the detection of a soluble antigen present in solution may be effected by the addition of an antibody specific for that antigen at sufficient concentrations to permit realization of the specific antigen-antibody reaction. The antigens and antibodies combine and form large insoluble aggregates which become visible as precipitates. Unfortunately, if the antigen is present only at low concentration levels, the resulting weak antigen-antibody reaction may not form a precipitate of sufficient size and quality to permit direct visible detection. In order to enhance the size of the precipitate and thereby aid in its detection, it has been found that the agglutination of antigen and an antibody linked with another particle such as an inert latex particle forms a significantly larger precipitate more clearly visible to the naked eye.

The agglutination immunoassay utilizing inert particles made from a latex or polystyrene polymer poses other problems. The polystyrene latex carrier particles are difficult to coat and standardize and additionally often give false results due to nonspecific reactions because of physical adherence by hydrophobic materials to the polystyrene latex carrier particles in aqueous media. Alternatively, erythrocytes, e.g. red blood cells, have been advantageously used as indicator particles since they are convenient passive carriers of antigens. There are numerous erythrocyte-linked antigen settling tests or passive hemagglutination assays which have succeeded primarily because the red blood cells can be preserved by chemical fixation and most antigens existing on the surface of the RBC can tolerate the chemical treatment without loosing their affinity to specific antibody. Additionally, antigens can often be chemically attached to red blood cells thus permitting a cross-linkage to an indicator particle subsequent to immunological reaction with the specific antibody.

These methods and principles have been described in publications such as "The Preparation and Use of Formalinized Erythrocytes with Attached Antigens or Haptens to Titrate Antibodies" by Joseph S. Ingraham, published in *Proc. Soc. Exp. Biol. Med.*, Vol. 99, 1958, p. 452–456; "The Use of a Water-Soluble Carbodiimide as a Coupling Reagent in the Passive Hemagglutination Test" by H. M. Johnson et al., published in the *Journal of Immunology*, Vol. 97, No. 6, 1966, p. 791–796.

There has, however, been little success in chemically linking antibodies to particles such as red blood cells without damaging the avidity of the antibody. For instance, the reverse passive hemagglutination assay (RPHA) reagent with antibody against hepatitis-B surface antigens (HBsAg) on aldehyde-fixed red blood cells for the diagnosis of hepatitis-B is an example of a test which met the requirements for "third generation" sensitivity of hepatitis tests in the U.S., however, not only is the test less sensitive than existing RIA hepatitis tests, but the resulting cell settling patterns are extremely difficult to read by those inexperienced in the techniques. One of the reasons for this is thought due to an inability to covalently link antibody onto chemically activated particles or cells with either control over the sites or the orientation of the immunoglobulin molecules on the surface. Thus, the antibody molecules are likely to have random orientation as well as multiple attachments on the carrier surface. Hence, the avidity of the antibody and its ability to form a lattice structure in agglutination is seriously impaired.

It is one of the objects of the present invention to provide a multiple or conjugate antibody reagent having an antibody linked to a carrier particle primarily by single attachment, thereby providing flexible orientation and minimal effect on conformation and another antibody of differing specificity free for further immunological reactions.

Use of multiple antibodies in the past has been essentially limited to head-to-tail combinations as compared to the present invention which combines antibodies in a substantially tail-to-tail fashion. For instance, U.S. Pat. No. 4,048,298 to Niswender teaches a procedure directed toward a solid phase double antibody competitive radioimmunoassay procedure wherein the antigenic substance or ligand is converted to a radioactive derivative and used to stimulate the production of antibodies. Thereafter a second antibody specific for the first antibody is produced. The second antibody may be immobilized onto a water insoluble organic polymeric substance or one having a polymeric nature. The second antibody is capable of reacting with the first antibody-antigen complex and converting all attached substances into an insoluble form. It is believed the activity of the second antibody is probably diminished because attachment by covalent bonding or physical adsorption is nonspecific and occurs with multiple attachment sites, resulting in distortion of the conformation and flexibility of the antibody molecule. Additionally, the use of radioisotopes presents problems which are preferably avoided. Specifically, these problems include (a) the relatively short life of gamma emitting isotopes (e.g. $^{125}$I), (b) impairment of immunological reactivity and specificity by gamma radiation of the isotope, (c) health hazards involved in the use of dangerous radioisotopes which necessitates the use of procedures complying with federal standards as well as requiring precise safety controls and (d) expensive, complex instrumentation such as scintillation counters.

The present invention has, as one of its objectives, the reduction of the complexity of the reagent, the test procedure, and the preferable avoidance of a radioisotope in order to accomplish a similar sensitivity.

The prior art has attempted to increase sensitivity using radioisotopes as described above as well as fluorescent and enzyme indicators and hybrid antibodies.

Multivalent hybrid antibodies have been produced previously and typical technology is reported in *Molecular Immunology*, Vol. 17, 1980, p. 395–401, in an article entitled *"Multivalent Hybrid Antibody"* by Ghetie and Mota. The publication describes the formation of a multivalent hybrid antibody having dual specificity using protein A of *Staphylococcus aureus* (SpA). The hybrid is made by immunoglobulin (IgG) reaction with SpA which is capable of linking the IgG molecules through their Fc portions. For example, anti-A and anti-B antibodies were reacted with SpA and formed a multivalent hybrid antibody having a molecular composition described as (IgG anti-A/SpA/IgG anti-B)$_2$. This reagent is not, however, suitable for agglutination tests or attachment to an indicator particle because of nonspecific agglutination which can be caused by the multivalent antibody of the hybrid in the presence of a single type of antigen. The present invention teaches the use of a univalent antibody such as an Fab' fragment of IgG for attachment onto carrier particles in order to avoid nonspecific agglutination. This is not possible with the Ghetie and Mota system since reaction with SpA requires the presence of the Fc portion of the immunoglobulin which portion is not present in a univalent Fab' fragment.

Nisonoff and Rivers, in *Archives of Biochemistry and Biophysics*, Vol. 93, 1961, p. 460–462, cited by Ghetie and Mota, describe the preparation of a univalent hybrid antibody molecule having dual specificity by the recombination of two Fab' fragments from the reduction of anti-A (Fab')$_2$ and anti-B (Fab')$_2$. Problems associated with this approach include random combination as well as interference by unwanted anti-A/anti-A and anti-B/anti-B recombinants. An object of the present invention includes the avoidance of these problems by the use of a hetero-bifunctional coupling reagent capable of conjugating two different specific immunoglobulins. Hetero-bifunctional coupling reagents have been described in the following publications: J. Carlsson et al., *Biochemistry Journal*, Vol. 173, 1978, p. 723–737; G. Ishikawa et al., *Enzyme Labeled Immunoassay of Hormones and Enzymes*, ed. S. B. Pal, 1978, p. 43–57; T. Kitagawa and T. Aikawa, *Journal of Biochemistry*, Vol. 79, 1976, p. 233–235; J. N. Limet et al., *Journal of Immunology Methods*, Vol. 28, 1979, p. 25–32; E. S. Rector et al., *Journal of Immunology Methods*, Vol. 24, 1978, p. 321–336; and S. Yoshitake et al., *European Journal of Biochemistry*, Vol. 101, 1979, p. 395–399.

"Lectin Immuno Test" by J. L. Guesdon and S. Avramas published in the *Journal of Immunological Methods*, Vol 39, 1980, p. 1–13 describes yet another possible method of detecting antigens utilizing fresh red blood cells as a marker. The publication discloses the use of a concanavalin A antibody conjugate which utilizes the combining sites present on lectin to bind the marker substance. The proposed method and reagent present certain disadvantages, among them the use of glutaraldehyde for coupling, thereby complicating the composition of the conjugate due to the covalent bonding nature of such a nonselective coupling method. Further, the lectin antibody conjugate is not suitable for the direct passive hemagglutination test and is limited only to solid phase immunoadsorption tests. The nonspecific hemagglutination occasioned by concanavalin A limits the application and sensitivity of this testing procedure.

Another system, utilizing fresh red blood cells as the immunoassay marker or indicator substance, devised for the determination of the presence of hepatitis antigen is described in "Immune Adherence Hemagglutination Test", by M. Mayumi et al., published in *Vox Sang*, Vol. 20, 1971, p. 178–181. The proposed method utilizes the principle that an antigen-antibody-complement complex has adherence to erythrocytes thus providing a hemagglutination test for hepatitis antigen. The disadvantages of this system are that complement fixation tests in general are not very stable, they are reversible, and they require great technical skill to perform.

In addition to the damage incurred to antibodies by aldehyde treatment as aforementioned, other problems include the rigidity of such fixed cells which limits intercellular contact to a few points thereby producing less force to hold the agglutinate matrix. In contrast, the fresh cells utilized in the present invention have large intercellular contact in numerous areas because of the flexible membrane and consequently exhibit superior holding of the matrix pattern. Thus, higher sensitivity can be reached in the present invention utilizing double antibody conjugate with fresh red blood cells as an indicator substance. A further problem encountered with aldehyde-treated cells is that they become increasingly hydrophobic which in turn causes spontaneous clumping or nonspecific agglutination. These considerations are explored by T. S. Ingraham in *Proc. Soc. Exp. Biol. Med.*, Vol. 99, 1958, p. 452–456.

Although the present invention has great utility as an agglutinating agent of red blood cells, it has the flexibility and capability of using other marker substances in substitution for red blood cells. Such substances include enzymes, radioisotopes, fluorochromes, electron opaque substances and polymeric microspheres which may incorporate fluorescent or nonfluorescent dye materials.

The first immunoglobulin may be selected for its affinity either directly to these marker substances or to another substance linked to the marker substance. The use of enzymes, radioisotopes or electron opaque substances will require more complex procedures and equipment than that necessitated by a red blood cell marker but may nonetheless be desired by the clinician in specialized circumstances.

In addition to those objects already mentioned, it is an object of this invention to provide a diagnostically useful reagent utilizing the double antibody conjugate as direct agglutinating agents useful for the detection of soluble antigens. It is another object of the invention to provide a reagent having maximum antibody avidity permitting the formation of a reagent capable of agglutinating with maximum sensitivity. It is another object of the invention to provide methods and materials which do not require highly specialized handling skills or complex and expensive equipment. It is yet another object of the present invention to provide materials and methods meeting the requirements for third generation sensitivity for hepatitis tests. It is still yet another objective of the present invention to provide a reagent capable of being used with fluorochromes, enzymes, erythrocytes, electron opaque substances, radioactive isotopes, as well as polymeric microspheres. It is another object to provide an agglutinating agent capable of using fresh erythrocytes obtained by the user or supplied in conjunction with the agglutinating agent. It is another object to provide a method for detecting the presence of a specified antigen in a water-soluble or aqueous sample.

SUMMARY OF THE INVENTION

In accordance with the objects of the present invention, diagnostically useful reagents comprising the selective conjugation of antibodies specific for different serological determinants for agglutination tests as well as methods of use are provided. More particularly, this invention relates to an immunoassay reagent for detecting an antigen comprising a first immunoglobulin having a defined specificity, a second immunoglobulin of different specificity then said first immunoglobulin and specific for the antigen to be detected and a hetero-bifunctional coupling reagent selectively coupling said first immunoglobulin to said second immunoglobulin. It is preferred that the defined specificity of the first immunoglobulin be selected so that it is useful for immobilizing or detecting the combination of reagent and antigen. To this end, it may be specific for antigens appearing on the surface of a substrate or particle or specific for a tag or indicator substance.

As used herein, selectively coupling means the hetero-bifunctional coupling reagent is capable of distinguishing and binding to one immunoglobulin over another immunoglobulin of differing specificity based upon the order of selection and availability of functional groups for binding the antibody to the coupling reagent; preferential selectivity of binding being governed in part by different binding coefficients.

Also provided is an immunoassay reagent for detecting an antigen and employing the use of an indicator substance comprising: a first immunoglobulin specific for an antigen naturally or artificially linked to said indicator substance; a second immunoglobulin specific for the antigen to be detected; and a hetero-bifunctional coupling reagent capable of providing a sulfhydryl-reactive functional group and an amine-reactive functional group and selectively coupling said first immunoglobulin to said second immunoglobulin. More specifically, this immunoassay reagent may have a hetero-bifunctional coupling reagent that is covalently bonded to said first immunoglobulin by the formation of a thiol bond and covalently bonded to said second immunoglobulin by the formation of an amide bond. In a preferred embodiment the hetero-bifunctional coupling reagent is soluble in a water miscible solvent and does not cause any substantial loss of avidity of said first and second immunoglobulins.

Additional embodiments of the immunoassay reagents as described include: those wherein said first immunoglobulin is the Fab' univalent fragment of IgG following pepsin digestion and dithiothreitol reduction (such a fragment is necessary in an agglutination system since a bivalent immunoglobulin would cause nonspecific agglutination); those wherein the indicator substance is an erythrocyte and said first immunoglobulin is specific for said associated antigens naturally present on the surface of said erythrocyte; those wherein the indicator substance is a fixed erythrocyte having associated antigens artificially planted on the surface and said first immunoglobulin is specific for said associated antigens; and those wherein the hetero-bifunctional cbupling reagent is a cross-linking reagent having an amine-reactive functional group selected from the group consisting of N-hydroxysuccinimide ester, p-nitrophenol ester and 1-hydroxy benzotriazole ester, and a sulfhydryl-reactive functional group selected from the group consisting of maleimide, iodoacyl and 2-pyridyldithio.

In preferred embodiments if the immunoassay reagents as described, the second immunoglobulin is a human or animal antihepatitis-B surface antigen immunoglobulin of either polyclonal or monoclonal origin; and the indicator substance is selected from the group consisting of erythrocytes, enzymes, radioisotopes, fluorochromes, electron opaque substance, and polymeric microspheres.

Also provided is an immunoassay reagent for detecting an antigen comprising an indicator substance having an associated antigen, a first immunoglobulin specific for said associated antigen, a second immunoglobulin specific for the antigen to be detected, and a hetero-bifunctional coupling reagent selectively coupling said first immunoglobulin to said second immunoglobulin.

Also provided is a method for detecting the presence of a specified antigen within an aqueous sample comprising the steps of: combining with said sample (a) an immunoassay reagent for detecting an antigen employing an indicator substance having an associated antigen comprising: a first immunoglobulin specific for said associated antigen, a second immunoglobulin specific for the antigen to be detected, and a hetero-bifunctional coupling reagent selectively coupling said first immunoglobulin to said second immunoglobulin, and (b) said indicator substance to form a mixture; agitating said mixture; allowing said mixture to settle undisturbed; and observing said mixture for the indicator substance whereby the presence of the antigen to be detected is indicated. Alternatively the indicator substance could have been added to the reagent prior to combining the reagents with the sample. A preferred embodiment provides for the indicator substance to be selected from the group consisting of erythrocytes and microspheres and the allowing to settle step includes observing said mixture for the existence of agglutination whereby the presence of the antigen to be detected is indicated. In another preferred embodiment for detecting the presence of a specified antigen within an aqueous sample, the method as described is employed wherein said indicator substance is an erythrocyte, said antigen to be detected is selected from the group consisting of human chorionic gonadotropin and hepatitis-B surface antigens; or wherein said second immunoglobulin is selected from the group of anti-human chorionic gonadotropin immunoglobulin, and anti-hepatitis-B surface antigen immunoglobulin, respectively, either immunoglobulin being of polyclonal or monoclonal origin.

Also provided is a method for detecting the presence of a specified antigen present on a surface comprising the steps of: contacting with said surface an immunoassay reagent for detecting an antigen and employing the use of an indicator substance comprising a first univalent immunoglobulin specific for said indicator substance, a second immunoglobulin specific for the antigen to be detected, and a hetero-bifunctional coupling reagent capable of providing a sulfhydryl-reactive functional group and an amine-reactive functional group and selectively coupling said first immunoglobulin to said second immunoglobulin; further contacting with said surface an indicator substance selected from the group consisting of erythrocytes, enzymes, radioisotopes, fluorochromes, electron opaque substances, and polymeric microspheres; allowing said reagent and said indicator substance to react; removing unreacted reagent and indicator substance; and examining said surface for the presence of said indicator particle whereby the existence of said specified antigen may be determined.

Further provided is a method for detecting the presence of a specified antigen present on a surface comprising the steps of: contacting with said surface an immunoassay reagent for detecting an antigen comprising an indicator particle having an associated antigen wherein the indicator substance is selected from the group consisting of erythrocytes, enzymes, radioisotopes, fluorochromes, and polymeric microspheres; a first immunoglobulin specific for said associated antigen, a second immunoglobulin specific for the specified antigen to be detected, and a hetero-bifunctional coupling reagent selectively coupling said first immunoglobulin to said second immunoglobulin; allowing said reagent to react with said surface; removing unreacted reagent and indicator particles; and examining said surface for the presence of said indicator particle whereby the existence of said antigen may be determined.

Further embodiments of the methods for detecting the presence of specified antigens specify the first immunoglobulin as a univalent immunoglobulin; or specify the antigen to be detected as present on tissue or as immobilized on a solid-phase substrate.

BRIEF DESCRIPTION OF THE DRAWINGS

Further understanding as well as additional objectives of the present invention will become clear upon examination of the drawings wherein:

FIG. 1 shows a simplified representation of the hetero-bifunctionally coupled antibody immunoassay reagent attached to a carrier particle in the presence of antigen.

FIG. 2 illustrates the use of the present invention in a solid-phase immunoadsorption test.

FIG. 3 demonstrates the use of the present invention for the identification of cell surface antigens.

FIG. 4 stylistically represents the formation of a lattice structure by use of the present invention in a hemagglutination test.

DESCRIPTION OF THE PREFERRED EMBODIMENTS

FIG. 1 shows a stylized representative view of the double antibody conjugate of the present invention attached to an indicator or carrier particle and the antigen to be detected. Specifically FIG. 1 shows an indicator particle or carrier substance 1 which contains on its surface, either artificially or naturally induced, an antigen for which antibody 2 is specific. Preferably antibody 2 will be univalent such as the Fab' fragment of IgG following pepsin digestion and dithiothreitol reduction so as to reduce nonspecific agglutination. A hetero-bifunctional coupling reagent 3 is used to covalently couple immunoglobulin 2 with the immunoglobulin 4 specific for the antigen 5 to be detected. Previously, proteins such as immunoglobulins have been covalently coupled by the use of homo-bifunctional reagents such as glutaraldehyde, diimidates, diisocyanates, diphenylazides, and dimaleimides, however these reagents are restricted to the reaction of two identical function groups, for instance, the amino, phenol and thiol groups on proteins. Consequently, these nonselective coupling reagents have incurred only limited success in immunological assay procedures because of intramolecular cross-linking, self-condensation, polymerization and resulting deterioration of the antibody avidities.

The present invention avoids these troublesome aspects by the use of a hetero-bifunctional coupling reagent 3 which is selectively reactive with different groups on proteins. The selective coupling aspect of the hetero-bifunctional coupling reagent avoids the formation of self-condensed products by forming an amide bond at one end of the reagent and a thiol bond at the other end. Each of these differing bonds can be used to link or conjugate different antibodies respectively. Further, the immunoglobulins can be intact or fragmented antibodies isolated from either human or animal sources. These antibodies may be of polyclonal origin or of monoclonal origin such as a mouse hybridoma cell line producing anti-HBsAg monoclonal antibodies. Of course, the higher the quality of the antibody in the sense of purity and avidity, the greater the specificity and sensitivity of the resulting reagent.

With further reference to FIG. 1, ideally the immunoglobulin protein 2, specific for the particle or carrier 1, is a univalent immunoglobulin or its Fab' fragment [Fab' is the univalent fragment of IgG (the immunoglobulin G as defined in *Bulletin of World Health Organizations*, Vol. 30, 1964, p. 447) following pepsin digestion and dithiothreitol (DTT) reduction]combined through the hetero-bifunctional coupling bridge 3 with another immunoglobulin 4 that may be either univalent, bivalent or multivalent as with IgM. The immunoglobulin 2 specific for the indicator or carrier substance is preferably univalent so that there will be a single attachment onto the indicator substance per double antibody conjugate in order to avoid nonspecific agglutination from premature interparticle lattice formation and also to permit a maximum amount of rotation or swing of the conjugated macromolecule on the particle surface. Thus, immunoglobulin 4 which is chosen for its specificity for the antigen 5 in question is ultimately linked to immunoglubulin 2 through the thiol bond substantially at the tail portion of immunoglobulin 2 and consequently, will be quite flexible in its ability to reorient and interact with the specific antigen in question.

The substantially tail-to-coupling reagent-to-tail orientation is additionally advantageous because any conformational change of immunoglobulin 4 due to steric hindrance encountered by close contact of the particle surface 1 is expected to be minimal. Since the binding sites of antibody 4, because of the extension of antibody 2 and the coupling reagent 3, are more likely to be exposed rather than staggered and hindered on the particle surface, as is characteristic of prior art descriptions of chemically attached antibodies, the double antibody conjugate coated particles envisioned will interact easily with their specific antigens and hold their lattice formation in direct agglutination. The particles ideally suited as indicators for the conjugate linked agglutination test include those particles having naturally occurring surface antigens [e.g., erythrocytes (RBCs)]as well as those particles having artificially planted antigens. Preferably, Rh negative type O erythrocytes are used to avoid hemagglutination caused by blood type immunoreactions.

The class of hetero-bifunctional reagents includes those chemicals having a sulfhydryl-reactive functional group, for instance, maleimide, iodoacetyl or a 2-pyridyldithio group and also an amine reactive functional group of active ester such as N-hydroxy-succinimide ester, p-nitrophenol ester, 1-hydroxybenzotriazole ester, and the like. Compounds bearing both of these types of reactive groups and preferably soluble in a water miscible solvent, for instance, dioxane, acetone or dimethylformamide, are suitable for the conjugation of antibodies. Preferably, the reagent or solvent should not result in significant denaturation or loss of avidity. Since the coupling reagents bearing these bifunctionally reactive groups are labile under various conditions including high temperature, the presence of bases and nucleophiles, these reagents are typically stored anhydrous at low temperatures (less than 0° C.) and are advantageously dissolved in appropriate solvents just prior to use.

Preferably, conjugation is performed in an aqueous medium buffered to a pH of 5.0 to 8.5 depending upon the specific coupling agent being used. The pH should be kept to 7.0 and below for those bearing a maleimide group but may rise up to 8.5 for those bearing an iodoacetyl (or iodoacyl) group. Conventional buffer systems such as phosphate buffered saline (PBS) or similar systems that do not contain nucleophiles, such as amine or mercaptan which compete for the amino or sulfhydryl groups on the immunoglobulins, are ideal for the conjugation reactions. Typically, the conjugation of two different antibodies, antibody 2 and antibody 4, is performed in a two-step process. The first step advantageously uses 10 to 20 molar excess of hetero-bifunctional coupling reagent at pH 7 to selectively react with at least one amino group, presumably the epsilon amino group of lysine, by the formation of an amide linkage, to one or more maleimide or iodoacetyl groups on the immunoglobulin molecule of antibody 4. After removal of excess coupling reagent, the maleimide or iodacetyl group-linked antibody 4 is ready for coupling via a sulfhydryl group on antibody 2. Ideally, the thiol group can be generated by reduction of the interchain disulfide or alternately, by removal of a thiol-acetyl group introduced on the macromolecule with S-acetylmercapto succinic anhydride. All excess reagents are to be preferably removed either by gel filtration or dialysis between the reaction steps. The first step, coupling the reagent to antibody 4, starts at 0° C. and typically is completed within two hours at room temperature. The second step, coupling the activated antibody 4 to thiolated antibody 2, generally requires in excess of 20 hours at reduced temperature (4° C). In order to advantageously maximize the yield of desired one-to-one ratio of double antibody conjugate i.e. antibody 2-antibody 4, there must be careful calculation and optimal handling of the coupling conditions. Reduction of multivalent antibodies such as IgM is preferably avoided and such immunoglobulins are ideally bound by amide linkages.

The advantageous molar ratio of the Fab' fragment (antibody 2) or IgG (antibody 4) to coupling reagent, ranges from 1.1:1 to 1.5:1. It is preferred that an excess of the Fab' component is used in the beginning of conjugation to insure high coupling efficiency because the self-condensation by oxidation of the Fab' sulfhydryl groups to disulfide competes with the alkylation reaction toward the maleimide or iodoacetyl linkage on IgG and additionally because typically the desired, specific antibody is present only in a fractional amount of the total immunoglobulin population since the antibody is of polyclonal origin. It is preferred that unbound antibody be removed (fractionation by gel filtration) in order to avoid competition and to achieve maximum sensitivity.

The coating of the indicator particle with a fractionated or unfractionated form of the conjugate is generally performed by incubating a 10% packed cell suspension with the conjugate antibody solution for 15 to 30 minutes at 37 ° C. or room temperature followed with three phosphate balanced saline (PBS) washes. The amount of conjugate laden on the red blood cells is ideally titrated for each ba the conjugate antibody solution for 15 to 30 minutes at 37° C. or room temperature followed with three phosphate balanced saline (PBS) washes. The amount of conjugate laden on the red blood cells is ideally titrated for each batch of conjugate in order to achieve an optimal density which will have great sensitivity but present no false positives when tested with an antigen standard. Particles coated with too high a density of proteins or IgG generally result in excessive stickiness and ultimately nonspecific aggregation. Thus, the immunoassay reagent has variable sensitivity, adjustable by the amount of conjugate loading.

Sensitivity adjustment may be desirable in cases of cross-reactivity, for example, in the detection of human chorionic gonadotropin (HCG) and the closely related gonadotropin lutinizing hormone (LH) which otherwise interferes. With respect to HCG, if the reagent has a sensitivity greater than 0.5 IU/ml, then false positive reactions are commonly associated. By decreasing the sensitivity, these false positive reactions, occasioned by the detection of LH rather than HCG, can be advantageously eliminated.

Test serum specimens have to be heat-inactivated (56° C. for 30 minutes) in order to destroy any complement present which would otherwise interfere with the hemagglutination test. Further, it is preferable that small test serum volumes, such as 5$\mu$l or a 1/10 dilution thereof, be used for better specificity and sensitivity. It has also been found preferable to include normal rabbit serum (about 0.5%) and bovine albumin (about 1% in the assay system for elimination or minimization of rheumatoid and heterophile reactions as well as to facilitate the specific agglutination. Additionally, sodium azide (0.02% to 0.1%) may be advantageously employed as a general preservative in all coupling or testing solutions.

The immunoassay test is ideally performed by mixing a drop of approximately 0.05 ml of double antibody conjugate-coated RBCs (0.5 to 1% cells) with a drop (about 0.05 ml) of test serum and a couple of drops (0.1 to 0.2 ml) of diluent. Allowing the mixture to aggregate on a slide permits a rapid determination (about 10 to 15 minutes) of the presence of antigen, however, this method is less sensitive. Although permitting the settling of the solution in a test tube or microtiter plate requires a greater duration of approximately two hours, such a method is preferable since greater sensitivity is achieved under these conditions. Positive reactions are typically indicated by cell aggregates on the slides or mats and rings on the bottom of the test tubes or microtiter plates while negative reactions are indicated by the lack of any visible aggregates on the slide test or the presence of buttons in the settling tubes or microtiter plates.

Occasionally, it has been found that an immunoassay utilizing hepatitis-B surface antigen (HBsAg) negative sera will give a small ring within two hours of settling. In order to avoid a false positive, one may have to prolong the settling period for an additional two hours whereupon the small rings from negative samples will generally shrink to buttons while those weak positives will remain in rings with a surrounding shadow of a mat. With respect to the detection of hepatitis-B surface antigen, of tremendous importance and advantage is that the present invention has a sensitivity of greater than 1 ng HBsAg/ml serum which exceeds the requirements of the third generation hepatitis-B test set by the U.S. Bureau of Biologics. The preferred embodiment of the double antibody conjugate employed in this immunoassay system is a chimpanzee anti-hepatis-B surface antigen immunoglobulin hetero-bifunctionally coupled to rabbit anti-human red blood cell fragment specific for and attached to human red blood cells, e.g. (CpXHBsAg) IgG-(RxhRBC) Fab' coated human RBC. Clearly the advantages of such a hepatitis test include the ability to detect soluble antigens with a method that is simple, sensitive, easily read, requires small samples and avoids false positives.

Another important area where the present invention demonstrates advantageous utility is its use as a diagnostic reagent to determine pregnancy. The presence of human chorionic gonadotropin is determined by mixing a drop of human Orr cells in PBS with a drop of urine or serum sample and the (RxHCG) IgG-(RxhRBC) Fab' conjugate where RxHCG is rabbit anti-human chorionic gonadotropin. The density of the conjugate laden on the cells must be adjusted to a sensitivity level of 0.5 IU HCG/ml of urine in order to avoid the interference by lutinizing hormone (LH) and follicle stimulating hormone (FSH) as previously described. The formation of a mat in a settling test tube after two hours is indicative of a positive reaction for the presence of a high level of HCG and therefore pregnancy.

Alternatively in FIG. 1, immunoglobulin 2 could be specific for the antigen 5, preferably immobilized on a substrate, and immunoglobulin 4 specific for an indicator substance other than erythrocytes since it is bivalent and nonspecific agglutination is preferably to be avoided.

FIG. 2 further illustrates the use of the present invention in a solid phase immunoabsorption test wherein an antigen 11 is immobilized upon a substrate 10 and to which is directed heterospecific conjugate antibody 12 which is additionally specific for the antigen in question 5. The portion of antibody conjugate 12 directed against immobilized antigen 11 is preferably univalent in order to maximize rotational and orientation capabilities but may be multivalent. Subsequently, the system is washed and then treated with a second group of conjugate antibodies 14 to which are attached indicator substance 1. Quantitation of the presence of indicator substance 1 will be representative of the amount of antigen 5 present in the test sample.

With reference to FIG. 3, the present invention employing a conjugated antibody reagent 14, comprising two different antibodies 21, 22 coupled tail-to-tail by a hetero-bifunctional coupling reagent and having an antibody 21 portion specific for an indicator substance 15, may be used to determine the presence of surface antigens present on tissue cells 20. Contemplated is the use of the present invention in the localization and determination of tumor cells having tumor specific surface antigens. In such a situation, it is expected that the antibody 22 specific for the tumor antigen will be of monoclonal origin.

FIG. 4 shows, in a preferred embodiment of the present invention, a stylized lattice formation in a hemagglutination test. The double antibody conjugate 14 has an Fab' fragment specific for a red blood cell indicator 16 and a multivalent antibody portion specific for the antigen to be detected 5. Presence of the antigen 5 permits multiple attachments of the conjugate 14 attached to blood cell 16. Consequently, the red blood cells are held in firm lattice formations in the form of mats which are clearly visible to the unaided eye.

The principles of the present invention can be further illustrated by, but are not limited to the following examples:

EXAMPLE 1

2.5 mg of affinity purified chimpanzee anti-hepatitis-B surface antigen immunoglobulin (CpxHBsAg IgG) dissolved in 2 ml of pH 7 phosphate buffered saline (PBS) is chilled in an ice bath and the N-hydroxy-succinimide ester of N-(4-carboxycyclohexymethyl) maleimide (55 μg, 10×molar excess), dissolved in peroxide free dioxene (0.1 ml), is added while stirring at 0° C. for 15 minutes and then at room temperature for one hour. Excess reagent is removed by gel filtration on a Sephadex G-15 (1.5×45 cm) column using deaerated pH 6.0 PBS with 1 millimolar EDTA as eluant. The chromatography is monitored by UV. Fractions of the first peak containing maleimide-IgG are pooled and maintained at 4° C. for conjugation with the Fab' fragment of rabbit anti-human red blood cells (RxhRBC). One mg of RxhRBC (Fab')$_2$ in 0.7 ml of pH 8.0, 0.01 molar tris buffered saline (TBS) is stirred under nitrogen while 1.0 mg of dithiothreitol (DTT) in 0.1 ml of H$_2$O is added. After 1 hour of stirring at room temperature, excess DTT is removed on a Sephadex G-15 (1.0×20 cm) column with deaerated pH 6.0 PBS-1 millimolar EDTA. The fractions containing Fab'-SH are pooled and mixed immediately under nitrogen with the maleimide CpxHBsAg IgG. The pH of the conjugation solution is adjusted with 1/40th volume of 1 molar pH 7.0 sodium phosphate and the reaction is run at 4° C. under nitrogen for approximately 20 hours. The resulting conjugate solution is filtered through a microfilter (0.22 microns) to a clear solution. Sodium azide is added as a preservative to a concentration of 0.1%. The unfractionated conjugate is suitable for coating human Orr RBCs as a direct agglutination reagent for testing for the presence of hepatitis. The ratio of conjugate to RBCs has to be titrated to a maximum sensitivity without causing nonspecific aggregation and is accomplished by the use of graduated positive and negative controls.

The conjugate is preferably packed into a diagnostic reagent test kit having two containers, one of which contains the buffered conjugate reagent and the other containing the diluent of 0.5% normal rabbit serum and 1% bovine albumin in PBS with 0.1% sodium azide. The conjugate reagent ideally has about 0.05 mg of double antibody protein per ml of PBS (pH 7.4, 0.1% sodium azide). Each drop (approximately 0.05 ml) of this reagent is titrated to coat one drop (approximately 0.05 ml) of 10% Orr RBCs (approximately $5 \times 10^7$ cells per ml) for 10 tests. Commercially available bloodbanking reagent cells or freshly drawn (within one week) Orr cells from a HBsAg free person are ideal carriers for the conjugate. The test is preferably carried out as follows:

1. Cell sensitization—Orr cells are washed three times and adjusted to 10% with PBS. One drop of the 10% cells is mixed with one drop of the conjugate reagent and incubated at 37° C. for at least 15 minutes. The cells are washed three times and suspended in PBS (with 0.02% sodium azide) to 0.5%. The coated cells are stable for at least three days in PBS at 4° C. storage.

2. Cell settling—one drop of the sensitized cells (approximately $2.5 \times 10^6$ cells) is added to a glass test tube ($1.0 \times 7.5$ cm) having 5 $\mu$l of patient's serum and two drops of diluent. Complete mixing is accomplished by shaking for one minute. The cells in the test tubes are left undisturbed to settle on a view mirror for two hours. Results are then observed. Agglutination in the form of a mat (positive) or ring (weak positive) is indicative of serum from a hepatitis-B infected person while nonagglutination, denoted by a button of cells at the bottom of the tube, is indicative of a serum negative for hepatitis-B.

EXAMPLE 2

Ten mg of QAE-Sephadex purified rabbit anti-human chorionic gonadotropin (RxhCG) IgG in two mls of pH 7.0 PBS chilled in an ice bath, is added to the N-hydroxysuccinimide ester of N-(4-carboxycyclohexylmethyl) maleimide (0.4 mg, 20× molar excess), dissolved in peroxide free dioxane (0.1 ml), while stirring at 0° C. for 15 minutes. The mixture is then removed to room temperature for one hour followed by gel filtration on a Sephadex G-15 ($1.5 \times 45$ cm) column with deaerated pH 6.0 PBS-1 millimolar EDTA. The fractions containing maleimide IgG are pooled and kept at 4° C, ready for conjugation. Four mg of RxhRBC (Fab')$_2$ suspended in 0.8 ml of pH 8.0 TBS is stirred under nitrogen at room temperature while DTT (2 mg) in 0.2 ml of H$_2$O is added. After one hour of stirring, excess DTT is removed by gel filtration on a Sephadex G-15 ($1 \times 30$ cm) column with deaerated pH 6.0 PBS-1 millimolar EDTA. The reduced Fab' is pooled and mixed immediately with the maleimide-(RxhCG) IgG and 1/40th volume of pH 7.0, 1 molar sodium phosphate buffer by stirring under nitrogen at 4° C. for approximately 20 hours.

The resultant conjugate mixture is filtered through a 0.45 micron filter and fractionated on a Sephacryl S-200 ($2.6 \times 75$ cm) column using pH 8.0 TBS to elute. Fractions of the major peak containing (RxhCG) IgG-(RxhRBC) Fab' conjugate are pooled. After titration against HCG standard, the concentration of the conjugate is adjusted to approximately 0.01 mg per ml.

The reagent may be advantageously packed into a diagnostic reagent kit which contains the conjugate (approximately 0.01 mg/ml) with 0.5% bovine albumin and 0.1% normal rabbit serum in PBS with 0.1% sodium azide. Ten ml of reagent are sufficient for 100 tests.

The test is carried out as follows:

Commercially available bloodbanking reagent or freshly drawn (within one week) human Orr cells are washed three times and diluted in PBS to 1%. One drop of the diluted cells are delivered into a glass test tube ($1.0 \times 7.5$ cm), then two drops of the conjugate reagent and one drop of serum or urine specimens are added with complete mixing by shaking for one to two minutes. The cells in the test tubes are left to settle undisturbed on a view mirror for two hours. The results are then observed. Agglutination in the form of a mat or diffused ring indicates high levels of human gonadotropins in the urine indicative of pregnancy; nonagglutination in the form of a button or small ring indicates low or normal levels of gonadotropins in the specimen.

Although the foregoing disclosures and examples illustrate the preferred embodiments of the invention, it will be understood that various alternatives will occur to those of ordinary skill in the art without departing from the spirit and scope of the invention herein.

We claim:

1. An immunoassay reagent for detecting an antigen comprising:
    (a) a first immunoglobulin;
    (b) a second immunoglobulin of different specificity than said first immunoglobulin and specific for the antigen to be detected; and
    (c) a hetero-bifunctional coupling reagent selectively coupling said first immunoglobulin to at least part of the interchain disulfide linkage of said second immunoglobulin.

2. An immunoassay reagent for detecting an antigen and employing the use of an indicator substance comprising:
    (a) a first immunoglobulin specific for said indicator substance;
    (b) a second immunoglobulin specific for the antigen to be detected; and
    (c) a hetero-bifunctional coupling reagent having a sulfhydryl-reactive functional group and an amine-reactive functional group, selectively coupling said first immunoglobulin to at least part of the interchain disulfide linkage of said second immunoglobulin.

3. An immunoassay reagent as described in claim 2 wherein said first immunoglobulin is the Fab' univalent fragment of IgG.

4. An immunoassay reagent as described in claim 2 wherein the hetero-bifunctional coupling reagent is
    (a) covalently bonded to said first immunoglobulin by the formation of a thiol bond; and
    (b) covalently bonded to said second immunoglobulin by the formation of an amide bond.

5. An immunoassay reagent as described in claim 4 wherein the hetero-bifunctional coupling reagent is soluble in a water miscible solvent and does not cause any substantial loss of avidity of said first and second immunoglobulins.

6. An immunoassay reagent for detecting an antigen comprising:
    (a) an indicator substance having an associated antigen;
    (b) a first immunoglobulin specific for said associated antigen;
    (c) a second immunoglobulin specific for the antigen to be detected; and (d) a hetero-bifunctional coupling reagent selectively coupling said first immunoglobulin to at least part of the interchain disulfide linkage of said second immunoglobulin.

7. An immunoassay reagent as described in claim 6 wherein the hetero-bifunctional reagent couples said first immunoglobulin to said second immunoglobulin by a thiol bond and an amide bond respectively.

8. An immunoassay reagent as described in claim 6 wherein said first immunoglobulin is the Fab' univalent fragment of IgG.

9. An immunoassay reagent as described in claims 7 or 8 wherein the indicator substance is an erythrocyte and said first immunoglobulin is specific for said associated antigens naturally present on the surface of said erythrocyte.

10. An immunoassay reagent as described in claim 7 or 8 wherein the indicator substance is a fixed erythrocyte and said first immunoglobulin is specific for said associated antigens artificially planted on the surface of said erythrocyte.

11. An immunoassay reagent as described in claim 7 or 8 wherein the hetero-bifunctional coupling reagent is a cross-linking reagent having an amine-reactive functional group selected from the group consisting of N-hydroxysuccinimide ester, p-nitrophenol ester and 1-hydroxy benzotriazole ester, and a sulfhydryl-reactive functional group selected from the group consisting of maleimide, iodoacyl and 2-pyridyldithio.

12. An immunoassay reagent as described in claims 2 or 6 wherein the second immunoglobulin is an immunoglobulin selected from the group consisting of chimpanzee anti-hepatitis-B surface antigen immunoglobulins, mouse monoclonal anti-hepatitis-B surface antigen immunoglobulins, and rabbit anti-human chorionic gonadotropin immunoglobulins.

13. An immunoassay reagent as described in claims 2 or 6 wherein the indicator substance is selected from the group consisting of erythrocytes, enzymes, radioisotopes, fluorochromes, electron opaque substances, and polymeric microspheres.

14. A method for detecting the presence of a specified antigen within an aqueous sample comprising the steps of:
(i) combining with said sample an immunoassay reagent for detecting an antigen comprising:
  (a) an indicator substance having an associated antigen;
  (b) a first immunoglobulin specific for said associated antigen;
  (c) a second immunoglobulin specific for the antigen to be detected;
  (d) and a hetero-bifunctional coupling reagent selectively coupling said first immunoglobulin to at least part of the interchain disulfide linkage of said second immunoglobulin;
(ii) agitating said combination;
(iii) allowing said agitated combination to settle undisturbed; and observing said combination for the indicator substance whereby the presence of said antigen is indicated.

15. A method for detecting the presence of a specified antigen within an aqueous sample comprising the steps of:
(i) combining with said sample
  (a) an immunoassay reagent for detecting an antigen employing an indicator substance having an associated antigen comprising: a first immunoglobulin specific for said associated antigen, a second immunoglobulin specific for the antigen to be detected, and a hetero-bifunctional coupling reagent selectively coupling said first immunoglobulin to at least part of the interchain disulfide linkage of said second immunoglobulin, and
  (b) said indicator substance;
(ii) agitating said combination;
(iii) allowing said agitated combination to settle undisturbed; and observing said combination for the indicator substance whereby the presence of the antigen to be detected is indicated.

16. A method for detecting the presence of a specified antigen as provided in claims 14 or 15 wherein the indicator substance is selected from the group consisting of erythrocytes and polymeric microspheres; and the allowing to settle step includes observing said combination for the existence of agglutination whereby the presence of said antigen is indicated.

17. The method of claims 14 or 15 wherein:
said indicator substance is an erythrocyte;
said antigen to be detected is selected from the group consisting of human chorionic gonadotropin and hepatitis-B surface antigens; and
the allowing to settle step includes observing said combination for the existence of agglutination whereby the presence of said antigen is indicated.

18. The method of claim 17 wherein:
said antigen to be detected is hepatitis-B surface antigen and said second immunoglobulin is selected from the group consisting of mouse monoclonal anti-hepatitis-B surface antigen immunoglobulin and chimpanzee anti-hepatitis-B surface antigen immunoglobulin.

19. A method for detecting the presence of a specified antigen present on a surface comprising the steps of:
(i) contacting said surface with an immunoassay reagent employing the use of an indicator substance comprising:
  (a) a first immunoglobulin specific for said indicator substance;
  (b) a second immunoglobulin specific for said antigen to be detected; and
  (c) a hetero-bifunctional coupling reagent having a sulfhydryl-reactive functional group and an amine-reactive functional group, selectively coupling said first immunoglobulin to at least part of the interchain disulfide linkage of said second immunoglobulin;
(ii) further contacting with said surface an indicator se interchain disulfide linkage of said second immunoglobulin;
(ii) further contacting with said surface an indicator substance selected from the group consisting of erythrocytes, enzymes, radioisotopes, fluorochromes, electron opaque substances, and polymeric microspheres;
(iii) allowing said reagent and said indicator substance to react;
(iv) removing unreacted indicator substance; and
(v) examining said surface for the presence of said indicator substance whereby the existence of said specified antigen may be determined.

20. A method for detecting the presence of a specified antigen present on a surface comprising the steps of:
(i) contacting said surface with an immunoassay reagent for detecting said specific antigen comprising;

(a) an indicator substance, having an associated antigen, and selected from the group consisting of erythrocytes, enzymes, radioisotopes, fluorochromes, electron opaque substances, and polymeric microspheres;
(b) a first immunoglobulin specific for said associated antigen;
(c) a second immunoglobulin specific for the specified antigen to be detected; and
(d) a hetero-bifunctional coupling reagent capable of selectively coupling said first immunoglobulin to at least part of the interchain disulfide linkage of said second immunoglobulin;

(ii) allowing said reagent to react with said surface;
(iii) removing unreacted reagent; and
(iv) examining said surface for the presence of said indicator particle whereby the existence of said specified antigen may be determined.

21. The method as described in claims 19 or 20 wherein said first immunoglobulin is a univalent immunoglobulin.

22. The method as described in claims 19 or 20 wherein said specified antigen to be detected is present on tissue.

23. The method as described in claims 19 or 20 wherein said specified antigen to be detected is immobilized on a solid-phase substrate.

* * * * *